Oct. 5, 1954
R. O. RUBEL, JR
Plant Pat. 1,308
CAMELLIA PLANT
Filed Sept. 16, 1953
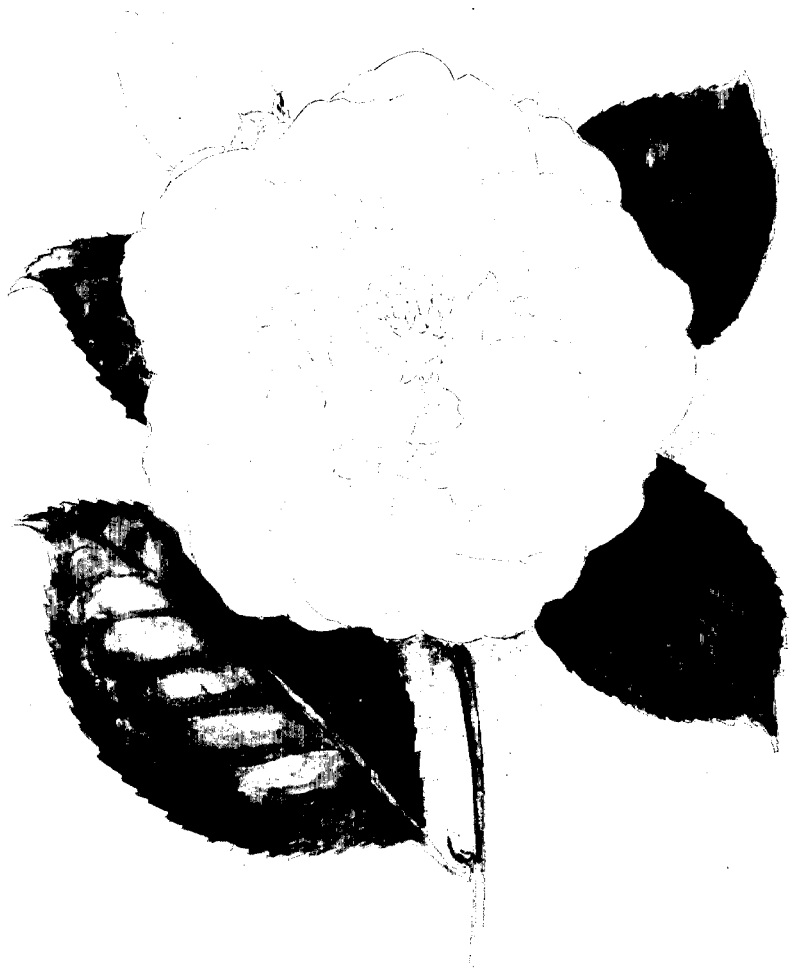
WITNESS
Addison E. Avery
INVENTOR
ROBERT O. RUBEL, JR.
by Rummler, Rummler & Snow,
ATTYS.

Patented Oct. 5, 1954

Plant Pat. 1,308

UNITED STATES PATENT OFFICE 1,308

CAMELLIA PLANT

Robert O. Rubel, Jr., Mobile, Ala., assignor to
Cliff Harris, Mobile, Ala.

Application September 16, 1953, Serial No. 380,635

1 Claim. (Cl. 47—60)

This invention relates to a new and distinct variety of *Camellia japonica*, which originated as a seedling of unknown parentage resulting from selection procedures directed by me and including the harvesting and planting in contiguity of seeds from selected plants. The original seedling of this variety was planted in 1932 at my nursery in Mobile. Alabama. It has been asexually reproduced from cuttings and grafting at Mobile, Alabama, through several generations and its characteristics appear to be permanently fixed.

This variety does not resemble any previously existing camellia known to me. Its large, crinkly, ruffled, light salmon rose to dark rose colored petals with crimped margins make it a spectacular bloom that has no comparison. The plant flowers in November out of doors at Mobile, Alabama, and continues blooming through February. It has continued to bloom and produce excellent flowers after enduring freezing weather unprotected outdoors. The plant is a compact and vigorous grower and its blooms have long-lasting quality, making it desirable for use as a florist's cut flower and as a corsage.

The accompanying painting shows the natural coloring and shapes of the blooms and foliage.

The color designations, according to Maerz and Paul's Dictionary of Color, are as follows:

| Part | Plate | Ltr. | No. |
|---|---|---|---|
| Flower: | | | |
| Lightest shade | 1 | A | 3 |
| shading into | 1 | I | 3 |
| shading into (darkest) | 3 | J | 4 |
| Leaves: | | | |
| Top leaf | 23 | L | 5 |
| Under side of leaf (not shown on drawing) | 22 | L | 6 |
| Stem | 7 | J | 11 |

The following is a detailed description of my new variety:

Origin: Seedling of unknown parentage.

Classification: *Camellia japonica.*

Flower: Recurrent: yes. Unicolored variable from light salmon to dark rose. Produces sports having petals variegated with blotches of white.

*Size.*—Maximum size 5 in. (12.5 cm.) in diameter, and 1⅞ in. (4.5 cm.) high.

*Borne.*—Singly and double.

*Shape.*—High center, incomplete double.

*Petalage.*—Approximately 77 petals and petaloids, including 10 large outer petals 2⅜ in. x 1⅞ in. (5.5 cm. x 4.5 cm.). Inner portion of bloom composed of irregular mass of petaloid, both large and small, intermixed with and joined to fascicle of stamens hidden among them.

*Form.*—Orbicular, attenuate at base, crinkly and ruffled with crimped margins.

*Color.*—Light salmon to dark rose.

*Texture.*—Leathery with satiny surface.

Affected by hot weather 60° or above.

Slight fragrance.

Lasting quality excellent as a plant and cut flower.

Stamens: Approximately 167 central and scattered in 4 or 5 fascicles among the petaloids. Filaments upright, colored yellow tint at their bases.

Pistil: Malformed with 5 styles, $\frac{9}{16}$–$1\frac{1}{16}$ in. long (1.2 cm. to 2.6 cm.).

Foliage:

*Leaves.*—Rigidly coriaceous, ovate, bases cuneate, apexes acute, blades approximately $3\frac{3}{16}$ to 4⅜ in. (8–11 cm.) long and 2 to 2⅜ in. (5–6 cm.) wide and slightly serrated edges.

Buds:

*Size.*—Large. $1\frac{3}{16}$ in. (3 cm.) long and $\frac{13}{16}$ in. (2 cm.) in diameter just before opening.

*Form.*—Elliptic ovoid.

*Color.*—Very light green.

*Sepals.*—7 to 10, hooded over bud.

*Calyx.*—Large and smooth.

Plant:

*Form.*—Round bush.

*Height.*—Depends on age.

*Growth.*—Vigorous, compact and branching.

I claim:

The new and distinct variety of camellia plant, substantially as shown and described, and characterized by the size, color and lasting quality of its flowers, having large, crinkly, ruffled petals with crimped margins, and the rigidly coriaceous leaves of its foliage.

No references cited.